United States Patent [19]

Yamada et al.

[11] Patent Number: 5,304,692
[45] Date of Patent: Apr. 19, 1994

[54] CATALYST COMPOSITION FOR DISPROPORTIONATION OF OLEFINS AND PROCESS FOR DISPROPORTIONATION OF OLEFINS USING THE SAME

[75] Inventors: Takao Yamada; Goro Sawada, both of Ichihara; Eiji Takahashi, Chiba, all of Japan

[73] Assignee: Maruzen Petrochemical Co., Ltd., Tokyo, Japan

[21] Appl. No.: 960,970

[22] Filed: Oct. 14, 1992

[30] Foreign Application Priority Data

Oct. 17, 1991 [JP] Japan .................................. 3-298435

[51] Int. Cl.$^5$ ................................................ C07C 6/04
[52] U.S. Cl. ...................................... 585/646; 585/643
[58] Field of Search ........................ 585/643, 651, 646

[56] References Cited

U.S. PATENT DOCUMENTS

| | | | |
|---|---|---|---|
| 3,445,541 | 5/1969 | Heckelsberg | 260/683 |
| 3,544,648 | 12/1970 | Wilson | 585/643 |
| 3,579,602 | 5/1971 | Reusser | 260/683 |
| 3,586,731 | 6/1971 | Heckelsberg | 260/683 |
| 3,673,114 | 6/1972 | Allum et al. | 585/643 |
| 3,707,579 | 12/1972 | Montgomery | 260/683 D |
| 3,760,026 | 9/1973 | Reusser et al. | 260/683 D |
| 3,786,112 | 1/1974 | Reusser et al. | 585/643 |
| 3,915,897 | 10/1975 | Reusser et al. | 260/683 D |
| 4,080,313 | 3/1978 | Whittam | 252/455 R |
| 4,575,575 | 3/1986 | Drake | 585/646 |
| 4,654,461 | 3/1987 | Drake et al. | 585/646 |

FOREIGN PATENT DOCUMENTS 7111882  5/1972  Netherlands .................. 585/643

*Primary Examiner*—Carl F. Dees
*Attorney, Agent, or Firm*—Melvin I. Stoltz

[57] ABSTRACT

A disproportionation catalyst for olefins and a process for disproportionation of olefins using said catalyst are disclosed. The catalyst is a mixture of one part by weight of a first catalyst component comprising silica gel carrying thereon a tungsten oxide or its precursor and a Group I metal oxide or a compound convertible to Group I metal oxide; and 8–75 parts by weight of a second catalyst component which is alumina having a specific surface area of 20–120 m$^2$/g, and preferably carrying thereon a Group I or Group III metal oxide or a compound convertible to such an oxide. It exhibits a remarkably extended life of disporportionation activity and is thus applicable to the industrial use. The catalyst, therefore, can produce industrially useful compounds at a low cost by the application of the olefin disproportionation.

11 Claims, No Drawings

CATALYST COMPOSITION FOR DISPROPORTIONATION OF OLEFINS AND PROCESS FOR DISPROPORTIONATION OF OLEFINS USING THE SAME

BACKGROUND OF THE INVENTION

1. Field of the Invention

The present invention relates to disproportionation of olefins, and, more particularly, to a novel catalyst system which is useful for disproportionation of olefins and to a process for disproportionation of olefins using such a catalyst.

2. Description of the Prior Art

Disproportionation (sometimes called metathesis) of olefins is defined as a reaction in which one or more olefins are converted into other olefins by the exchange of alkylidene groups as shown in the following formula:

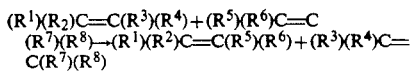

(In the formula, $R^1$, $R^2$, $R^3$, $R^4$, $R^5$, $R^6$, $R^7$ and $R^8$ are independently selected from the group consisting of a hydrogen atom and an alkyl group.)

This reaction was first discovered by Banks and Bailey in 1964 in a reaction in which ethylene and 2-butene are produced from propylene in the presence of a molybdenum catalyst. The discovery has led to successive developments of various disproportionation catalysts, including molybdenum-, tungsten-, and rhenium-type catalysts. However, several problems still remain to be solved concerning with the application of the disproportionation process to the manufacture of industrially useful products with a high purity at a low cost. Some problems which are to be solved are (1) promotion of the selectivity by suppressing isomerization and polymerization reactions, (2) reduction of the induction period which results improvement in the conversion rate and shortening of start-up time, (3) prolongation of the catalyst life by suppressing loss or denaturation of active sites of catalysts which is caused by changes in the valency of metals due to water, dienes or oxygen-containing substances contained in raw materials or in by-products, or by suppressing accumulation of carbonaceous materials contained in by-products onto the catalysts, and the like.

A number of catalyst systems and reaction methods have been proposed in efforts for overcoming these problems. As regards to the above-described problem (1), for example, a method of adding an alkaline metal oxide to a disproportionation catalyst, e.g., to tungsten oxide catalyst carried by silica gel, was disclosed in U.S. Pat. No. 3,579,602 and U.S. Pat. No. 3,586,731; and a method of using a mixed catalyst system in which magnesium oxide or the like is combined with a disproportionation catalyst was disclosed in U.S. Pat. No. 3,707,579. Other catalyst systems combining these catalysts, e.g., MgO+WO3/SiO2(KOH), were proposed in U.S. Pat. No. 3,915,897, U.S. Pat. No. 3,760,026 and U.S. Pat. No. 4,575,575.

As regards to the problem (2) above, a brief explanation is given below. In the disproportionation reaction of olefins, long induction period results a poor conversion rate. The reason therefor is that during the induction period, i.e., prior to the commencement of disproportionation reaction, poisonous reaction by-products attack the active sites of the catalyst, and carbons and resinous polymeric materials accumulate onto the surface or active sites of the catalyst which markedly impair the catalyst activity even after the completion of the induction period. In the disproportionation reaction of olefins, it is necessary that the valency of tungsten in the active catalyst should be kept in a specific range, and therefore, the existence of induction period is inevitable due to the time required for changing the valency of tungsten contained in the catalyst to the specific range. Method heretofore proposed for overcoming the above-described problem (2) by subjecting the catalyst to a reducing treatment by hydrogen or carbon monoxide prior to use is well known.

With respect to the problem (3), U.S. Pat. No. 3,707,579 disclosed a method of extending the catalyst life by passing hydrocarbon feed stocks through a pre-activated magnesium oxide bed (a guard bed) to remove poisonous components such as water, dienes, oxygen-containing compounds, and the like contained in the starting raw materials.

None of these methods, however, cannot solve all the above-mentioned problems at the same time. For example, the method disclosed in the above U.S. Pat. No. 4,575,575 which utilizes a mixed catalyst system comprising a disproportionation catalyst in which an alkaline metal oxide is combined with magnesium oxide or the like, is insufficient for industrial use because of its short catalyst life due to a rapid decrease in the conversion rate over time, even though it exhibits a significant effect on the promotion of the selectivity.

SUMMARY OF THE INVENTION

The present invention provides solutions to these problems. As a result of extensive studies to solve the aforementioned problems, the present inventors have found that a disproportionation catalyst having a remarkably prolonged catalyst life and a high disproportionation efficiency when compared to conventional disproportionation catalysts can be obtained by mixing (a) the first catalyst component which comprises silica gel, as a major component, carrying thereon a specific amount of tungsten oxide or its precursor and a specific amount of a Group I metal oxide or a compound convertible to the Group I metal oxide, and (b) the second catalyst component which comprises alumina having a specific surface area of a limited range, at a specified ratio by weight. This finding has led to the completion of the present invention.

Accordingly, the first object of the present invention is to extend the disproportionation catalyst life sufficiently for industrial use by providing a catalyst with a specific composition.

The second object is to provide a disproportionation catalyst giving a high disproportionation yield.

The third object is to provide a process for disproportionation reaction of olefins suitable for industrial use.

Other and further objects, features and advantages of this invention will appear more fully from the following descriptions.

Thus, the gist of the first invention resides in a disproportionation catalyst for olefins comprising, (a) the first catalyst component which comprises a silica gel having a $SiO_2$ purity of 99% by weight or higher and a specific surface area of 100 $m^2/g$ or more, as a carrier, carrying thereon tungsten oxide or its precursor in an amount of 1 to 10% by weight (calculated as oxide of the total amount of said first catalyst component and a Group I metal oxide or a compound convertible to the Group I metal oxide in an amount of 0.01 to 2% by weight (calculated as oxide) of the total amount of said first catalyst component and (b) the second catalyst component which comprises an alumina having a specific surface area of 20 to 120 $m^2/g$ and carrying thereon either (i) a Group I metal oxide or a compound convertible to the Group I metal oxide in an amount of 0 to 3.0% by weight (calculated as oxide) of the total amount of said second catalyst component or (ii) a Group III metal oxide or a compound convertible to the Group III metal oxide in an amount of 0 to 5.0% by weight (calculated as oxide) of the total amount of said second catalyst component, in an amount of 8 to 75 parts by weight per 1 part by weight of said first catalyst component; and the gist of the second invention resides in a process for disproportionation of olefins using said disproportionation catalyst.

DETAILED DESCRIPTION OF THE INVENTION

As the first catalyst component (a), silica gel is used as a carrier carrying thereon a tungsten oxide or its precursor and a Group I metal oxide or a compound convertible to the Group I metal oxide.

A high purity and high surface area silica gel for use as a catalyst carrier with a $SiO_2$ purity of 99% by weight or higher and a specific surface area of 100 $m^2/g$ or more, preferably 200 $m^2/g$ or more can be used as the carrier silica gel in the present invention. The shape and the size of the silica gel are not particularly limited. Broken, spherical or any other shapes can be used, with preferred being a spherical one with a size between 5 and 20 mesh (JIS sieve) which corresponds to outer diameter of about 4 to 0.8 mm.

A liquid for treating the above-described silica gel to carry tungsten oxide thereon may be a solution or a suspension of tungsten oxide or a tungsten compound which can be converted to the tungsten oxide through calcination. Tungsten compounds which can be used include, for example, the oxides, sulfides, halides, oxyhalides, tungstic acids and salts thereof, polytungstates, heteropolytungstates, peroxytungstates, and the like, and a mixture of these. Specific examples are tungsten trioxide, tungsten trisulfide, tungsten pentabromide, tungsten tetrachloride, tungsten hexafluoride, tungsten dioxydichloride, metatungstic acid, orthotungstic acid, ammonium metatungstate, ammonium phosphotungstate, and the like, and mixtures thereof.

The amount of tungsten oxide or its precursor to be carried on silica gel can be selected arbitrarily from a wide range, although 1 to 10% by weight (calculated as oxide) based on the total amount of the first catalyst component is particularly preferable for ensuring a good catalyst activity for disproportionation and a high selectivity of the target products.

As a Group I compound to be carried on the silica gel, oxides, hydroxides, carbonates, hydrogencarbonates, nitrates, acetates, and a mixture of these can be used. Among these, hydroxides are preferable from the aspect of their abundant availability, ease of handling, and a low price. Among hydroxides, potassium hyroxide and sodium hydroxide are particularly preferred. The amount to be carried on the silica gel may be 0.01 to 2% by weight (calculated as Group I metal oxide), and more preferably 0.1 to 1% by weight, based on the total amount of the first catalyst component. These tungsten and Group I metal compounds can be carried onto the silica gel either by preparing two separate solutions; one solution containing a suitable tungsten oxide or its precursor and the other containing a suitable Group I metal oxide or a compound which can be converted to the Group I metal oxide, and treating the silica gel sequentially with each solution, or, alternatively, by treating the silica gel with a single solution which contains both of these catalytically active components, i.e., tungsten oxide or its precursor and a suitable Group I metal oxide or a compound which can be converted into the Group I metal oxide in a single step. A better effect can be obtained if the treatment with these solutions is carried out after washing of the silica gel with water and drying it, as a pretreatment process.

As a method of treatment, various methods well known in the art for impregnating a carrier with a solution containing catalytically active components can be applied. Such methods include, for example, the adsorption method in which a treating solution is fed to a glass filter, in which silica gel is placed, to adsorb the active component, or the silica gel is charged into the treating solution, followed by removal of the excess solution by decantation or filtration; the evaporation-to-dryness method in which the silica gel is immersed in the solution and the mixture is allowed to stand to evaporate the solvent to dryness; and the spray method in which a solution containing a prescribed amount of active components is sprayed onto the silica gel. Furthermore, the pore-filling method in which the silica gel is contacted with a treating solution in an amount sufficient to be fully absorbed by the silica gel and wet it thoroughly, i.e., an amount approximately equal to or a little more of the total volume of pore cavities of the silica gel, can also be used. In all methods mentioned above, the silica gel must be kept in close contact with the solution for a sufficient perioģ of time in order for a precise amount of the active components to be carried uniformly onto the silica gel. It is therefore desirable that the silica gel be kept in the treating solution for several minutes to several hours with or without stirring after the impregnation. Following the impregnating procedure with the treating solution, the excess solution is removed by decantation, filtration, evaporation or any other suitable methods, and then the silica gel is dried by removing the solvent contained therein by a conventional drying method such as heating in furnace, a treatment in a dry-gas stream, a vacuum treatment, or a combination of these. Finally, the silica gel is calcined for 15 minutes to 24 hours at a temperature between 350° and 700° to convert tungsten compounds and/or Group I metal compounds into oxides. In general, the higher the temperature is, the shorter can be the time required for the calcination; the lower the temperature is, the longer is the time.

A catalyst with a high disproportionation activity can be prepared by the above-described procedure. However, this first catalyst component easily loses its activity in a short period of time when used singly, and hence regeneration of the catalyst is required in every few minutes to several hours or frequent replacement of the catalyst is necessary.

The alumina used as the second catalyst component of the present invention has a specific surface area of 20 to 120 $m^2g$, and preferably 70 to 100 $m^2/g$. In general, alumina is obtained from a hydrated alumina by a heat treatment and classified into several types according to the crystal structure. Besides α(alpha) type which is an entirely dehydrated and stable form, 7 metastable forms are known to exist which occur during the heating process; they are κ(kappa), θ(theta), δ(delta), γ(gamma), δ(eta), χ(chi) and ρ(rho). These 8 aluminas can be distinguished by their X-ray diffractiometry, although not all of their structures are distinctly identified. Either one of these metastable forms is produced according to the kind of the hydrate and conditions of the heat treatment. It is eventually transformed to α-type via other transitional forms when subjected to a higher temperature. The transition temperature may considerably differs depending on the sample history and the atmosphere of the heat treatment. Furthermore, surface characteristics of alumina such as the specific surface area and the pore size distribution may also vary depending on the heat treatment conditions. When treated at a temperature between 300° and 800° C., the metastable alumina has a fairly large specific surface area; i.e., as large as 100 to 600 $m^2/g$, but it decreases as the heat treatment temperature is raised higher.

in the present invention, these 8 aluminas can be used individually or as a mixture of two or more. When used individually, χ-alumina is most preferred. χ-Alumina can be prepared from fine particles of a hydrated alumina, commonly called gibbsite, through a heat treatment at 300° C. in the air. χ-Alumina is not a common carrier for conventional catalysts or oxidized metal catalysts due to its low activity as compared to that of γ or η-alumina. It is known that the specific surface area of α-alumina is in the range of several $m^2/g$, while that of γ or η-alumina, which are most widely used individually as a catalyst or as a carrier of oxidized metal catalysts for isomerization of olefins, is known to be 120 $m^2/g$ or more. In this regard, these kinds of aluminas do not satisfy the specified range for the specific surface area of the present invention; i.e., that of α-alumina is too small while that of γ- or η-alumina is too large. Both fail to be a suitable material for the second catalyst component of the present invention when used individually.

There are no specific limitations as to the shape and size of the alumina used as a component of the second catalyst. Cylindrical, spherical or any other shapes can be used, although preferred may be a spherical one having an outer diameter of about 6 to 0.8mm. The method for molding the alumina is not also particularly limited. In order to facilitate the molding of alumina, any known binders such as alumina cement or the like can be added.

The use of the above-described alumina as a sole second catalyst component can ensure the effect of keeping the disproportionation catalytic activity of the first catalyst component consistently stable for a long period of time. Furthermore, the selectivity can be improved by suppressing side reactions if a compound selected from Group I metal oxides, Group III metal oxides, and compounds convertible to one of these oxides, preferably a compound selected from oxides of potassium, sodium, thallium and compounds convertible to one of these oxides, is added to the alumina. Such an addition leads to a further extension of the life of the disproportionation catalytic activity. When adding a compound of Group I metal oxide or a compound convertible to the Group I metal oxide, the amount to be added is not greater than 3.0% by weight, e.g., 0.01 to 3.0% by weight, calculated as an oxide, based on the total weight of the second catalyst component. Similarly, when adding a compound of Group III metal oxide or a compound convertible to the Group III metal oxide, the amount to be added is not greater than 5.0% by weight, e.g., 0.01 to 5.0% by weight, calculated as oxide, based on the total weight of the second catalyst component. The same treatment solution and method as used in the treatment of the first catalyst component can be applied to the addition of a Group I metal oxide or a compound convertible to the Group I metal oxide to alumina in the second catalyst component. When a Group III metal oxide or a compound convertible to its oxide is added to alumina in the second catalyst component, a solution of oxide, hydroxide, sulfide, halide, nitrate, sulfate, carbonate, acetate, oxalate, or a mixture thereof may be used with a similar treating method as in the case of Group I metal compound.

The first and the second catalyst components are used after complete mixing at a ratio of 8–75 parts by weight of the second catalyst component per 1 part by weight of the first catalyst component. If the value is recalculated to volume ratio, the volume of the second catalyst component is 5 to 30 times of the volume of the first catalyst component. When the mixing ratio is smaller than this range, the selectivity and the life of the catalyst activity unfavorably decreases. On the other hand, a ratio greater than this range is not feasible dueto requirement of a too large reaction vessel, even though theoretically no problem is anticipated. When these two catalyst components are mixed and placed in a reaction vessel, it is important and advantageous for ensuring a longer disproportionation activity of the catalyst to keep each particle of the first catalyst component entirely surrounded by the second catalyst component so as to avoid mutual contact between the first catalyst component particles. For this purpose, it is desirable that particles of the first and the second catalyst components be made approximately the same size. Another technique to ensure this effect is to pulverize and thoroughly mix the first and the second catalyst components and mold the mixture into another shape such as pellets, tablets, extruded form, etc. Any other methods suitable to homogeneously mix the two catalyst components may also be applicable.

Activation treatments are conventionally practiced in the industry to activate disproportionation catalysts prior to use. Such conventional treatments are also applicable to the catalyst of the present invention. For example, a catalyst bed comprising the first and second catalyst components mixed together may be heated at 300° to 700° C. for 1 to 30 hours while flowing an oxygen-containing gas, and then flowing a reducing gas such as carbon monoxide, hydrogen or hydrocarbon at 300° to 700° C. for 0 to 120 minutes. This treatment will enhance the activity of the catalyst before use.

When the activity of the catalyst become lowered after the use for a certain period of time, a similar activation treatment can restore the catalyst activity and enables the catalyst to be used repeatedly for many times. In the catalyst system of the present invention, however, the catalyst activity can be easily restored after stopping the operation by simply flowing an inert gas such as nitrogen gas or the like through the catalyst bed for 10 minutes to 24 hours under any arbitrary pressure, and usually under the atmospheric pressure while keeping the temperature at the reaction temperature.

On the other hand, water and oxygen-containing compounds are known as catalyst poisons which decrease the activity of disproportionation catalysts. It is thus desirable to remove these compounds from feed stocks before feeding to a reaction vessel. A commonly known method of removing catalyst poisons contained in the hydrocarbon feed stock which may cause the decrease in the catalyst activity, such as water, dienes and oxygen-containing compounds, is a method of pretreating the feed stock before feeding to the reaction vessel by passing it through a dryer or a previously activated magnesium oxide bed (e.g., U.S. Pat. No. 3,707,579).

Olefins to be disproportionated in the present invention may be any $C_3$-$C_{12}$ olefin hydrocarbon, a mixture of two or more of such olefins, or a mixture of such olefins and ethylene. Examples of $C_3$-$C_{12}$ olefins include propylene, 1-butene, 2-butene, isobutylene, isobutylene dimer (a mixture of diisobutylene isomers, i.e., a mixture of 2,4,4-trimethylpentene-1 and 2,4,4-trimethylpentene-2), isobutylene trimer, 1-pentene, 2-pentene, isoamylene, 1-hexene, neohexene, heptenes, octenes, nonenes, and the like. When the feed stock is a mixture of such olefins and ethylene, the molar ratio of ethylene to olefin hydrocarbons is preferably about 2–4.

Disproportionation reactions are generally carried out at a temperature between 20° and 500° C. However, in the present invention, the reaction temperature is preferably set between 200° and 450°, and more preferably 300° to 400° C., in order to ensure a good conversion rate within a relatively short reaction time. Reaction pressure can also be selected from a wide range, but preferably from a range between 10 and 40 atm.

The disproportionation reaction can be carried out in any phases, including a liquid phase, a gaseous phase, or a mixed phase containing a diluent. This reaction can be carried out either in batch-wise or continuously. The catalyst of the present invention can be used in any suitable forms such as dispersed forms, fixed beds, fluidized beds, moving beds, and the like. Among them, the most preferred one is a continuous process by the use of fixed bed flow method.

The disproportionation reaction of the present invention can be carried out at a wide range of raw material charge rate. For example, raw materials can be charged in a weight hourly space velocity (WHSV) of 0.3–180 hr$^{-1}$, and preferably 3.6–90 hr$^{31\ 1}$ in which WHSV is calculated by raw material charge rate (g/hr) per weight of the first catalyst component (g). When the disproportionation reaction of isobutylene dimer with ethylene is taken as an illustration, isobutylene dimer can preferably be charged in a liquid hourly space velocity of 0.1–50 hr$^{-1}$, and more suitable range is 1–25 hr$^{-1}$ on the basis of the volume of the first catalyst component, if the reaction temperature is set within a range of 200°–450°°C.

Other features of the invention will become apparent in the course of the following description of the exemplary embodiments which are given for illustration of the invention and are not intended to be limiting thereof.

DESCRIPTION OF THE PREFERRED EMBODIMENTS

Example 1

This example demonstrates preparation of catalysts.

A first catalyst component was prepared by impregnating 1 g of silica gel of high purity and high specific surface area [Cariact-10: Trade name, a product of Fuji-Devison Chemical Co., Ltd., $SiO_2$ purity 99.8%, specific surface area 280 m$^2$ g, particle size 10–20 mesh (diameter 0.8–2mm)] with 1.1 g of an aqueous solution of active components comprising 0.15g of an ammonium metatungstate concentrate (a product of Nippon Inorganic Colour & Chemical Co. Ltd., 50% by weight solution calculated as $WO_3$) and 0.003 g of potassium hydroxide. The impregnated silica gel was dried at 110° C. for 24 hours, gradually heated up, and calcined at 530° C. for 6 hours. Eventually, the first catalyst component was confirmed to contain 7% by weight of $WO_3$ and 0.25% by weight of $K_2O$.

A second catalyst component was prepared by impregnating a prescribed amount of an aqueous potassium hydroxide solution into high purity $\chi$-alumina (a product of Nissan Girdler Catalyst Co., Ltd., specific surface area 86 m$^2$/g, $Al_2O_3$ purity 99.0%, particle diameter 2–4mm, spherical). The impregnated alumina was dried at 110°C. for 24 hours, then gradually heated up, and calcined at 530°for 6 hours.

A series of second catalysts each containing 0.3, 0.5, 1.0, 2.0 and 5.0% by weight of $K_2O$ were prepared by the process as described above. These catalysts are hereinafter designated as 0.3 $K_2O$-$\chi$, 0.5 $K_2O$-$\chi$, 1.0$K_2O$-$\chi$, 2.0$K_2O$-$\chi$ and 5.0$K_2O$-$\chi$, respectively.

For comparison, another catalyst was prepared in the same manner as above by using $\gamma$-alumina (a product of Nikki Chemical Co., Ltd., specific surface area 166 m$^2$/g, $Al_2O_3$ purity 99.7%) to which 1.0% by weight of $K_2O$ was impregnated. This catalyst is designated as 1.0 $K_2O$-$\gamma$.

Example 2

This example demonstrates preparation of catalysts.

Another second catalyst component was prepared in the same manner as in Example 1 by using $\chi$-alumina and an aqueous solution of thallium I nitrate instead of the potassium hydroxide solution. This catalyst, which contained approximately 1.0% by weight of $Tl_2O$ on the total weight of said second catalyst component, is designated as 1.0 $Tl_2O$-$\chi$.

Example 3

An experiment for preparation of neohexene by disproportionation of ethylene and diisobutylene was carried out using catalysts prepared in Example 1. Ethylene and diisobutylene were fed from the upper part of a vertically installed straight tube reactor (inner diameter 25 mm, length 700 mm and reacted by passing downward through the catalyst layer.

Raschig rings (porcelain) were packed up to about 25 cm height from the bottom flange of the reactor and, on the top of the raschig chips, a well-blended mixture of 3.7 g (about 10 ml) of the first catalyst component [$WO_3$/$SiO_2$($K_2O$)] and 70.9 g (about 100 ml) of the second catalyst component (1.0 $K_2O$-$\chi$) were placed. The height of the catalyst layer was 24 cm. Raschig rings were again packed in the space over the catalysts. Glass-wool was packed at boundaries of each layer.

Before the commencement of the reaction, air was passed through the catalyst layer at a rate of 100 ml/minute at 530°C. for about 5 hours and then carbon monoxide gas was passed for about 1 hour at a rate of 20 ml/minute at the same temperature. The temperature of the catalyst layer was then lowered by introducing nitrogen gas and the reaction was commenced when the temperature reached 370° C. The reaction pressure was kept at 28 Kg/cm$^2$G.

Ethylene was supplied from a bomb in a gaseous state and subjected to the reaction after passing through a dryer in which molecular sieve 13X was packed. Diisobutylene (DIB) was first refined by distillation, passed through a dryer in which molecular sieves 4A was packed, and further passed through a guard bed of magnesium oxide, before it was subjected to the reaction. The DIB was supplied at a rate of 40ml/hour. This amount approximately corresponds to 4 hr$^{-1}$LHSV (Liquid Hourly Space Velocity) based on the volume of the first catalyst component. Ethylene was supplied 4 times (in molar ratio) as much as DIB).

A specified amount of each reactant was introduced into a gas chromatograph analyzer by an automatic gas sampler every 30 minutes for analysis. The results of the reaction are summarized in Table 1. The DIB conversion rate, neohexene selectively, neohexene yield shown in Table 1 were calculated by the following formulae:

Reacted $DIB$ Moles = {([Neohexene]/84 + [Isobutene]/56 + [C$_6$ Isomers]/84)/2} + [C$_8'$]/112

Conversion Rate (%) =

$$\frac{\text{Reacted } DIB \text{ Moles} \times 100}{\text{Reacted } DIB \text{ Moles} + [\text{Unreacted } DIB]/112}$$

Selectivity (%) = $\frac{[\text{Neohexene}]/84 \times 100}{\text{Reacted } DIB \text{ Moles}}$ Yield (%) = (Conversion Rate × Selectivity)/100

In the above formulae, [Neohexene], [Isobutene], and [Unreacted DIB] are values expressed by their weight percents in the total reaction mixture measured by the gas chromatographic analysis. [C$_6$Isomers] is the total amount (wt. %) of C$_6$ olefins other than neohexene, e.g., 2,3-dimethylbutene, which were produced in the reaction. [C$_8'$] is the total amount (wt. %) of the products other than the raw material DIB, detected by the gas chromatographic analysis in the neighborhood of the peak corresponding to DIB and thereafter. The detected reaction products, other than neohexene, isobutene, C$_6$ isomers, unreacted DIB and C$_8'$, were unreacted ethylene and a small amount of propylene.

TABLE 1

| Reaction time (hours) | DIB Conversion Rate (%) | Neohexene Selectivity (%) | Neohexene Yield (%) |
|---|---|---|---|
| 2 | 97.4 | 87.8 | 85.6 |
| 4 | 96.6 | 88.3 | 85.3 |
| 6 | 96.3 | 90.5 | 87.1 |
| 8 | 96.0 | 90.6 | 87.0 |
| 10 | 96.3 | 89.0 | 85.7 |
| 12 | 95.7 | 91.7 | 87.7 |

TABLE 1-continued

| Reaction time (hours) | DIB Conversion Rate (%) | Neohexene Selectivity (%) | Neohexene Yield (%) |
|---|---|---|---|
| 14 | 94.6 | 93.7 | 88.7 |
| 16 | 95.0 | 91.2 | 86.6 |
| 18 | 94.6 | 92.3 | 87.3 |
| 20 | 94.1 | 87.8 | 82.6 |
| 25 | 90.4 | 93.2 | 84.3 |
| 30 | 90.5 | 87.6 | 79.3 |
| 35 | 85.6 | 88.6 | 75.8 |
| 40 | 81.5 | 92.5 | 75.4 |
| 45 | 81.1 | 82.3 | 66.8 |
| 50 | 74.0 | 81.5 | 60.3 |
| 55 | 71.1 | 78.9 | 56.1 |
| 60 | 70.0 | 74.6 | 52.3 |
| 65 | 68.2 | 71.4 | 48.7 |

Examples 4–7

Reactions were carried out under the same conditions as in Example 3, except that 0.3 K$_2$O-$\chi$, 0.5K$_2$O-$\chi$, 2.0 K$_2$O-$\chi$, and $\chi$-alumina (a product of nissan Girdler Catalyst Co., Ltd., specific surface area 86 m$^2$g, Al$_2$O$_3$ purity 99.0%, particle diameter 2–4 mm, spherical) were used, respectively, instead of 1.0 K$_2$ O-$\chi$ in example 3. The results are shown in Table 2, in which the maximum neohexene yield is the highest yield value, detected by the gas chromatographic analysis, among samples taken in every 30 minutes during the reaction and the catalyst life is the reaction time (hour) until the yield decreases below 50%. The definitions of maximum neohexene yield and catalyst life are also applicable to the following Examples and Comparative Examples.

Example 8

A reaction was carried out under the same conditions as in Example 3, except that 75.6 g (about 100 ml) of the 1.0 Tl$_2$ O-$\chi$prepared in Example 2 was used as the second catalyst component instead of 1.0 K$_2$ O-$\chi$ used in Example 3. The results are shown in Table 2.

Comparative Examples 1–5

Reactions were carried out under the same conditions as in Example 3, except that 40.1 g (about 50 ml) of $\gamma$-alumina (a product of Nikki Chemical Co., Ltd., specific surface area 166 m$^2$/g, Al$_2$O$_3$ purity 99.7%), 82.3 g (about 100 ml) of 1.0 K$_2$O-$\gamma$, 104.5 g (about 100 ml) of $\alpha$-alumina (AM-S34: Trade name, a product of Fujimi Kenmazai Kogyo, specific surface area 5 m$_2$/g, Al$_2$O$_3$ purity 99.8%), 74.6 g (about 100 ml) of 5.0 K$_2$ O-$\chi$and 100.9 g (about 100 ml) of MgO were used as the second catalyst component. The results are shown in Table 2.

TABLE 2

| No. | Component of Second Catalyst | Specific Surface Area m$^2$/g | Mixed Amount g (ml) | Maximum Neohexene Yield % | Catalyst Life hrs. |
|---|---|---|---|---|---|
| Examples | | | | | |
| 4 | 0.3 K$_2$O-$\chi$ | 89 | 73.1 (100) | 80.3 | 46 |
| 5 | 0.5 K$_2$O-$\chi$ | 83 | 70.8 (100) | 85.7 | 57 |
| 6 | 2.0 K$_2$O-$\chi$ | 78 | 73.5 (100) | 85.3 | 34 |
| 7 | $\chi$-Alumina | 86 | 67.9 (100) | 68.8 | 38 |
| 8 | 1.0 Tl$_2$O-$\chi$ | 79 | 75.6 (100) | 84.5 | 42 |
| Comparative Examples | | | | | |
| 1 | $\gamma$-Alumina | 166 | 40.5 (50) | 3.4 | 0 |
| 2 | 1.0 K$_2$O-$\gamma$ | 125 | 82.3 (100) | 17.7 | 0 |
| 3 | $\alpha$-Alumina | 5 | 104.5 (100) | 81.1 | 18 |
| 4 | 5.0 K$_2$O-$\chi$ | 75 | 74.6 (100) | 73.2 | 4 |

TABLE 2-continued

| No. | Component of Second Catalyst | Specific Surface Area m²/g | Mixed Amount g (ml) | Maximum Neohexene Yield % | Catalyst Life hrs. |
|---|---|---|---|---|---|
| 5 | MgO | 99 | 100.9 (100) | 78.3 | 28 |

\* The amount of the first catalyst component: 3.7 g (10 ml)
\*\* Catalyst life: The reaction time until the yield decreases below 50%.

Comparative Examples 1–3 are examples in which the second catalyst components have specific surface areas outside the scope of the present invention. In Comparative Example 4, although the second catalyst component has a specific surface area within the scope of the present invention, its $K_2O$ content is above the amount specified in the present invention. It is clear that all these catalysts have the catalyst lives extremely shorter than those in Examples 3–8. Comparative Example 5, which represents an example using MgO, which is conventionally considered to be an especially excellent catalyst, also exhibited a short catalyst life.

Example 9

A reaction was carried out under the same conditions as in Example 3, except that 35.1 g (about 50 ml) of 0.3 $K_2O$-$\chi$ was used as the second catalyst component. The results are shown in Table 3.

Comparative Example 6

A reaction was carried out under the same conditions as in Example 3, except that 7.5 g (about 10 ml) of 0.3 $K_2O$-$\chi$ was used as the second catalyst component. The results are shown in Table 3.

It is clear from the results that the catalyst life is extremely short when the ratio of the second catalyst component to the first catalyst component is smaller than the value specified by the present invention.

TABLE 3

| No. | Component of Second Catalyst | Specific Surface Area m²/g | Mixed Amount g (ml) | Maximum Neohexene Yield % | Catalyst Life hrs. |
|---|---|---|---|---|---|
| | | | Example | | |
| 9 | 0.3 $K_2O$-$\chi$ | 86 | 35.1 (50) | 76.0 | 32 |
| | | | Comparative Example | | |
| 6 | 0.3 $K_2O$-$\chi$ | 86 | 7.5 (10) | 70.1 | 8 |

\* The amount of the first catalyst component: 3.7 g (10 ml)
\*\* Catalyst life: The reaction time until the yield decreases below 50%.

The reaction was carried out under the same conditions as in Example 3, except that a mixture of 11.1 g (about 30 ml) of the first catalyst and 217.5 g (about 300 ml] of 0.3 $K_2O$-$\chi$, as the second catalyst, were placed in a straight tube reactor (inner diameter 38 mm, length 850 mm) from about 25 cm up to about 55 cm (the length of the catalyst layer: 29 cm), from the bottom flange, and further that the activation treatment of the catalyst with CO gas was carried out at 60 ml/min for 60 minutes, DIB was fed at a rate of 120 ml/hour, and the reaction temperature was 360°C. The results are shown in Table 4.

TABLE 4

| Reaction time (hours) | DIB Conversion Rate (%) | Neohexene Selectivity (%) | Neohexene Yield (%) |
|---|---|---|---|
| 5 | 94.6 | 76.6 | 72.5 |
| 10 | 94.6 | 79.2 | 74.9 |
| 15 | 91.9 | 86.6 | 79.6 |
| 20 | 89.3 | 86.5 | 77.3 |
| 25 | 88.1 | 86.2 | 76.0 |
| 30 | 85.9 | 89.6 | 77.0 |

TABLE 4-continued

| Reaction time (hours) | DIB Conversion Rate (%) | Neohexene Selectivity (%) | Neohexene Yield (%) |
|---|---|---|---|
| 35 | 82.5 | 92.1 | 76.0 |
| 40 | 83.5 | 90.5 | 75.3 |
| 45 | 79.9 | 92.6 | 74.0 |
| 50 | 77.4 | 93.5 | 72.3 |
| 55 | 74.1 | 89.0 | 66.0 |
| 60 | 68.5 | 91.7 | 62.8 |
| 65 | 61.5 | 91.7 | 56.4 |
| 70 | 58.0 | 90.5 | 52.5 |
| 75 | 55.2 | 91.3 | 50.4 |
| 80 | 52.8 | 90.2 | 47.6 |

A disproportionation catalyst for olefins is provided according to the present invention by using a first catalyst component comprising a silica gel, as a major component, carrying thereon tungsten oxide or its precursor and a Group I metal oxide or a compound convertible to the Group I metal oxide, and an alumina having a specific surface area of a limited range, as a second catalyst component, mixed with the first catalyst component at a specific ratio by weight. This catalyst exhibits a remarkably extended life of disproportionation activity and is thus applicable to the industrial use. The catalyst can also afford a higher disproportionation yield, if suitably composed so as to promote the selectivity and the conversion rate. The catalyst of the present invention, therefore, can produce industrially useful compounds at a low cost by the application of the olefin disproportionation.

Obviously, numerous modifications and variations of the present invention are possible in light of the above teachings. It is therefore to be understood that within the scope of the appended claims, the invention may be practiced otherwise than as specifically described herein.

What is claimed is:

1. A process for disproportionation of olefins characterized by contacting one or more olefin hydrocarbons having 3 to 12 carbon atoms or a mixture of said olefins and ethylene with a disproportionation catalyst comprising
   (a) the first catalyst component which comprises a silica gel having a $SiO_2$ purity of 99% by weight or higher and a specific surface area of 100 m²/g or more, as a carrier, carrying thereon tungsten oxide or its precursor in an amount of 1 to 10% by weight calculated as oxide of the total amount of said first catalyst component and a Group I metal oxide or a compound convertible to the Group I metal oxide in an amount of 0.01 to 2 % by weight calculated as oxide of the total amount of said first catalyst component and b) the second catalyst component which comprises an alumina having a specific surface area of 20 to 120 m$^2$/g and carrying thereon either (i) a Group I metal oxide or a compound convertible to the Group I metal oxide in an amount of 0 to 3.0% by weight calculated as oxide of the total amount of said second catalyst component or (ii) a Group III metal oxide or a compound convertible to the Group III metal oxide in an amount of 0 to 5.0% by weight calculated as oxide of the total amount of said second catalyst component, in an amount of 8 to 75 parts by weight per 1 part by weight of said first catalyst component.

2. A process for disproportionation of olefins according to claim 1, wherein said disproportionation reaction is carried out at a reaction temperature of 200°–450° C..

3. A process for disproportionation of olefins according to claim 1, wherein said process is carried out by the use of fixed bed flow method.

4. A process for disproportionation of olefins according to claim 1, wherein said olefin hydrocarbons are ethylene and isobutylene dimer.

5. A process for disproportionation of olefins according to claim 2, wherein said process is carried out by the use of fixed bed flow method.

6. A process for disproportionation of olefins according to claim 5 wherein said olefin hydrocarbons are ethylene and isobutylene dimer.

7. A process for disproportionation of olefins according to claim 6, wherein said isobutylene dimer is charged at a liquid hourly space velocity of 0.1–50 hr$^{-1}$ on the basis of the volume of said first catalyst component.

8. A process for disproportionation of olefins according to claim 7, wherein said Group I metal oxide in the first catalyst component is a potassium compound or a sodium compound, and said Group I metal oxide and Group III metal oxide or said compound convertible to these oxide in the second catalyst component is a potassium compound, a sodium compound, or a thallium compound.

9. A process for disproportionation of olefins according to claim 8, wherein said alumina is χ- alumina having a specific surface area of 70 to 100 m$^2$/g and said silica gel contained in said first catalyst component has a specific surface area of 200 m$^2$/g or higher.

10. A process for disproportionation of olefins according to claim 1, wherein said Group I metal oxide in the first catalyst component is a potassium compound or a sodium compound, and said Group I metal oxide and Group III metal oxide or said compound convertible to these oxide in the second catalyst component is a potassium compound, a sodium compound, or a thallium compound.

11. A process for disproportionation of olefins according to claim 10 wherein said alumina is χ-alumina having a specific surface area of 70 to 100 m$^2$/g and said silica gel contained in said first catalyst component has a specific surface area of 200 m$^2$/g or higher.

* * * * *